United States Patent [19]

Brown

[11] Patent Number: 5,147,368
[45] Date of Patent: Sep. 15, 1992

[54] NUCLEUS SPLITTER

[76] Inventor: Alan W. Brown, 4 Hartley Cir., Apt. 824, Owings Mills, Md. 21117

[21] Appl. No.: 680,888

[22] Filed: Apr. 5, 1991

[51] Int. Cl.⁵ ............................................. A61B 17/00
[52] U.S. Cl. .................................. 606/107; 294/99.2; 606/205; 606/210
[58] Field of Search ............... 606/107, 127, 128, 190, 606/205–211; 81/302, 416; 294/99.2

[56] References Cited

U.S. PATENT DOCUMENTS

| | | | |
|---|---|---|---|
| 3,254,649 | 6/1966 | Wood | 606/205 |
| 4,462,404 | 7/1984 | Schwarz et al. | 606/206 |
| 4,785,810 | 11/1988 | Baccala et al. | 606/107 |
| 4,844,065 | 7/1989 | Faulkner | 606/107 |
| 5,002,554 | 3/1991 | Korber | 606/207 |
| 5,014,407 | 5/1991 | Boughten et al. | 606/209 |

FOREIGN PATENT DOCUMENTS

| | | | |
|---|---|---|---|
| 0214727 | 10/1909 | Fed. Rep. of Germany | 606/207 |
| 0081549 | 10/1920 | Fed. Rep. of Germany | 606/207 |
| 0035357 | 3/1930 | France | 606/208 |
| 0356460 | 6/1938 | Italy | 606/210 |

Primary Examiner—Stephen C. Pellegrino
Assistant Examiner—Glenn Dawson
Attorney, Agent, or Firm—Diller, Ramik & Wight

[57] ABSTRACT

The invention is directed to a nucleus splitter adapted to crack a hard nucleus of an eye after the nucleus has been sculpted by a pair of crossed grooves which set-off four quadrants of the nucleus. The nucleus splitter includes a pair of arms having first and second end portions united at a pivot with each end portion terminating in a relatively elongated narrow member having a laterally projecting nucleus splitting tip. The second end portions of the arms are generally resilient and normally urge the narrow members and tips into abutment with each other along the plane through an axis of the pivot. Finger and thumb pressure is applied to the medial portion of the arms causing the elongated narrow members to rock, pivot or spread apart and in doing so define an acute angle opening away from the pivot. In this position the elongated narrow members and the entirety of the first and second arms remain on the same side of the plane as in the unstressed condition of the medial portion.

9 Claims, 1 Drawing Sheet

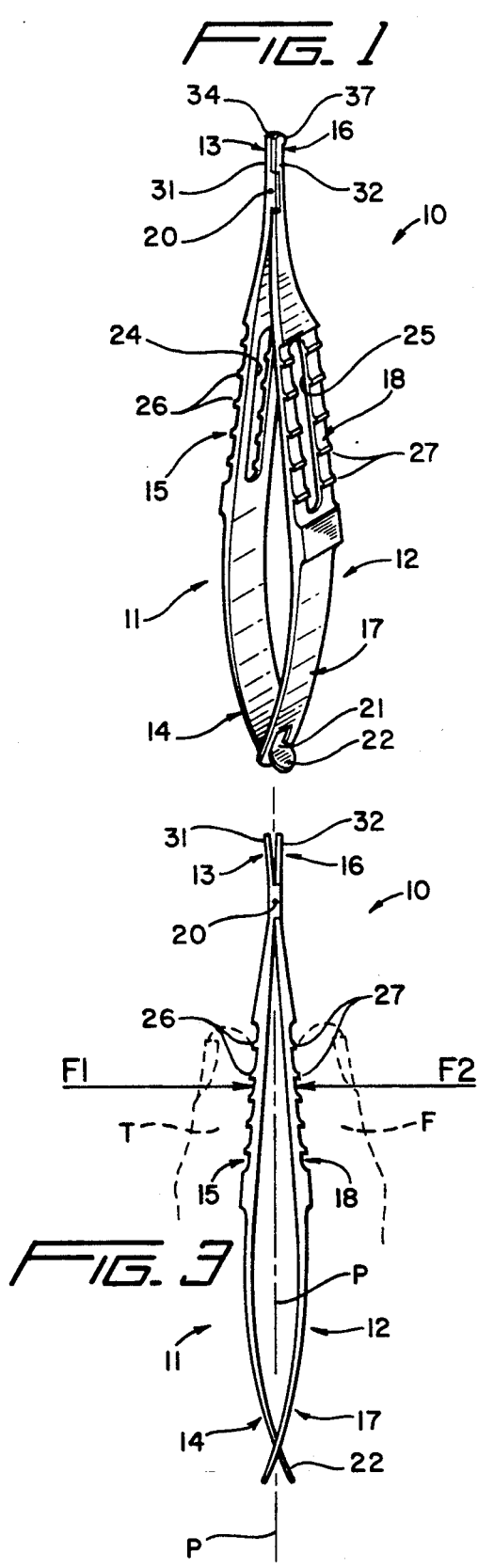
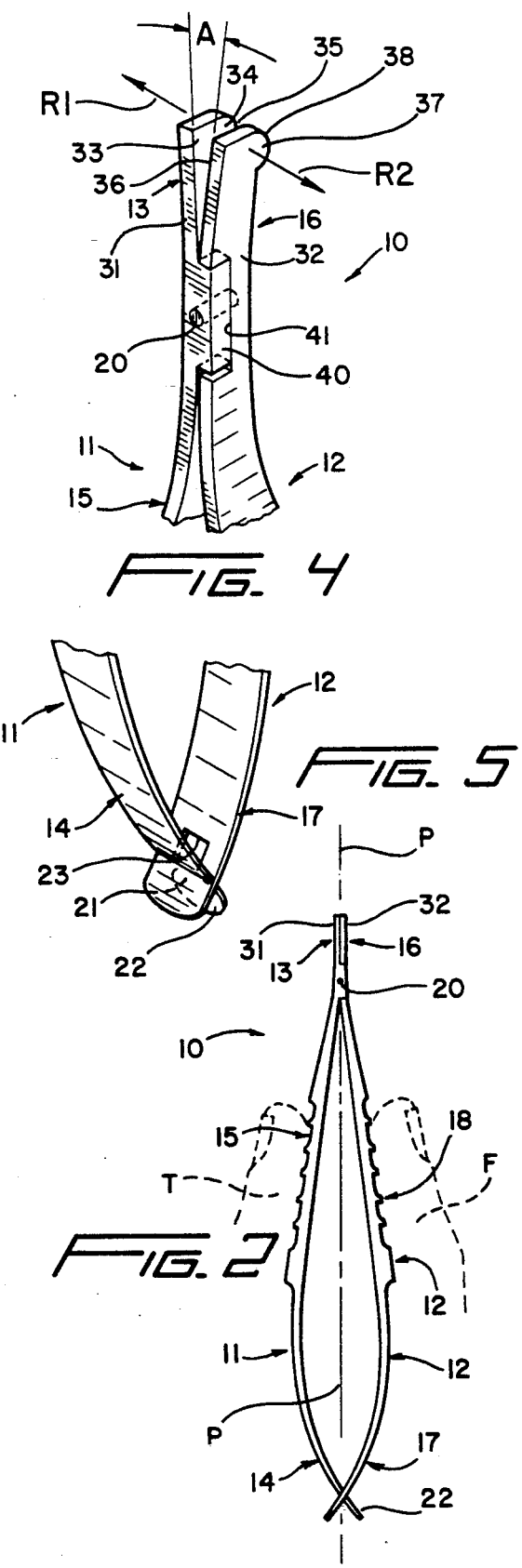

NUCLEUS SPLITTER

BACKGROUND OF THE INVENTION

In the area of cataract surgery, there exists a method of small incision lens removal utilizing ultrasonic energy termed phacoemulsification. This use of a small incision allows more rapid visual recovery for the method but also makes this method technically more difficult, especially with patients with advanced cataracts containing a hard nucleus.

A newer variant of the phacoemulsification method attempts to make removal of harder lens nuclei safer and simpler by fractionating the nucleus into four separate quarters or quadrants before phacoemulsification and aspiration. This method accomplishes fractionation by sculpting two V-shaped crossing grooves into the nucleus to set-off four generally equal sized quadrants. The phacoemulsification instrument is then inserted in the groove to provide a central to peripheral force which is opposed by a similarly placed second instrument positioned in the eye through a separate smaller incision. The two opposing forces result in the splitting of the nucleus into two which are in turn similarly split to yield four quarters. This fractionation technique makes the challenging phacoemulsification part of the procedure safer, but requires the use of two instruments and the added skills needed to manipulate these instruments to split the lens nucleus.

The fractionation technique can be accomplished with one instrument in the form of cross-action forceps manufactured by Rhein Medical of Tampa, Fla. These forceps disadvantageously require a large incision or wound for entrance into the eye and to accomplish fractionation because the arms spread a considerable distance in order to spread the lens cracking paddles. Additionally, these forces require multiple introduction and removals of the phacoemulsification instrument from the eye before complete four quadrant fractionation can occur. The additional instrument introduction and removals place the eye at higher risk for complication, such as iris injury, stripping of descemets membrane and even rupture of the posterior lens.

SUMMARY OF THE INVENTION

The present invention maintains the benefits of the fractionation technique and avoids the drawbacks of the prior art heretofore described.

Pursuant to the present invention, the nucleus splitter is formed by a pair of arms having first and second opposite end portions, a pivot connecting the two end portions to each other and a medial portion between the pivot and the second end portions. The second end portions are joined to each other by a sliding connection, and the second end portions and the medial portion impart flexibility to the nucleus splitter such that the first end portions are normally maintained closed or in abutment with each other. This abutment takes place between opposing surfaces of relatively elongated narrow members and associated splitting tips thereof when the arms are in a first unstressed condition. However, opposite forces are applied to the medial portions of the arms to cause the elongated narrow members and the tips thereof to progressively pivot or rock about the pivot forming a narrow acute angle opening away from the pivot and progressively spreading the tips as the opposing forces are applied to the medial portions. Accordingly, when the tips have been inserted in a sculpted groove of a nucleus and the forces thereafter applied as just described, the tips apply opposite forces to the sculpted groove(s) resulting in nucleus splitting or cracking.

Advantageously the nucleus splitter can be inserted into the eye through a relatively small incision because of the narrow or thin nature of the elongated narrow members and the fact that the pivot therebetween prevents lateral movement or spreading except for the extremely small acute angle opening heretofore defined. Therefore, the incision will not be spread open as opposite forces are applied to the medial portions of the arms and otherwise damage to the eye is precluded.

The elongated narrow members are also provided one with a generally rectangular guiding boss and the other with a generally rectangular guiding groove which cooperatively prevent lateral motion while assuring accurate pivoting to additionally preclude eye damage.

With the above and other objects in view that will hereinafter appear, the nature of the invention will be more clearly understood by reference to the following detailed description, the appended claims and the several views illustrated in the accompanying drawings.

BRIEF DESCRIPTION OF THE DRAWINGS

FIG. 1 is a perspective view of the nucleus splitter of the invention, and illustrates first and second arms each having first, medial and second end portions and a pivot between the first and medial portions.

FIG. 2 is a side elevational view of the nucleus splitter, and in phantom outline illustrates a thumb and forefinger holding the nucleus splitter prior to applying opposing forces thereto.

FIG. 3 is a view similar to FIG. 2, and illustrates opposing forces being applied to medial portions of the arms to cause elongated narrow members and laterally projecting nucleus splitting tips thereof to be spread or pivoted apart from each other.

FIG. 4 is a highly enlarged fragmentary perspective view of the first end portion and pivot of the nucleus splitter, and illustrates the elongated narrow members in their pivoted or opened position.

FIG. 5 is a fragmentary perspective view of the second end portions of the arms, and illustrates a sliding connection therebetween.

DESCRIPTION OF THE PREFERRED EMBODIMENT

A novel nucleus splitter constructed in accordance with this invention which is adapted to crack a hard nucleus of an eye is generally designated by the reference numeral 10.

The nucleus splitter 10 includes a pair of arms 11, 12 each made from titanium, stainless steel or like relative flexible metallic material. The arm 11 includes a first end portion 13, an opposite second end portion 14 and a medial portion 15 therebetween. The second arm 12 includes a first end portion 16, an opposite second end portion 17, and a medial portion 18 therebetween. Pivot means or a pivot 20 unites the first and second arms 11, 12, respectively, between the first portions 13, 16 and the medial portions 15, 18.

The second end portion 14 of the arm 11 includes a relatively narrow neck 21 and an enlarged generally circular head 22 which are confined for movement relatively to a polygonal or square opening 23 of the second end portion 17 of the second arm 12.

The medial portions 15, 18 of the arms 11, 12 include longitudinal slots 24, 25, respectively, and outboard of each are a plurality of pairs of ribs or ridges 26, 27, respectively. The ribs or ridges 26, 27 assure a good grip when the nucleus splitter 10 is grasped between a thumb T (FIGS. 2 and 3) and forefinger F of the surgeon. FIG. 2 illustrates the thumb T and finger F lightly gripping the nucleus splitter 10 without applying any force thereto, other than the light force necessary to grasp the nucleus splitter 10. However, as will be described more fully hereinafter, opposing forces F1 are shown applied to the respective medial portions 15, 18 of the respective arms 11, 12 by the thumb T and forefinger F when it is desired to pivot or rock apart the first end portions 13, 16 during splitting or fracturing of an associated nucleus, as will be described more fully hereinafter.

Referring specifically to FIG. 4, the first end portions 13, 14 each include relatively narrow elongated members 31, 32, respectively. The member 31 includes a face or surface 33 and a laterally projecting splitting tip 34 having a relatively rounded or convex surface 35. The elongated narrow member 32 likewise includes a relatively flat abutment surface 36 and a laterally projecting splitting tip 37 having a rounded or convex surface 38. The elongated member 31 also has a generally longitudinally elongated rectangular guiding boss 40 which is seated in a generally rectangular laterally opening guiding groove 41 of the elongated narrow member 32. The pivot 21 unites the elongated narrow members 31, 32 to each other for pivoting or rocking movement, and opposite ends (unnumbered) of the pivot or pivot pin 21 are suitably upset (flattened) to assure relatively pivoting movement in the absence of any type of lateral or longitudinal movement. Lateral and longitudinal movement is also prevented by the relative guidance provided through the inter action of the guide boss 40 and the guide groove 41. The unification of the elongated narrow members 31, 32 provided by the pivot 21, the guide boss 40 and the guide groove 41 assures that upon the application of the forces F1, F2, only pivoting movement will occur between the elongated narrow members 31, 32 which in turn assures that a nucleus will be split under optimum conditions without tear of the associated incision or opening through which the tips 34, 37 and the elongated narrow members 31, 32 have been introduced into the eye or otherwise cause damage to the eye. Normally in a first position of the arms 11, 12 when no force is applied to the arms in any fashion, the abutment surfaces 34, 36 of the respective elongated narrow members 31, 32 contact or abut each other along a plane P (FIG. 2) which passes through the axis of the pivot 21. It is to be noted that the arm 11 lies substantially entirely to the left of the plane P (FIGS. 2 and 3), while the arm 12 lies substantially to the right of the plane P (FIGS. 2 and 3). Exceptions to the latter is the slight projection of the boss 40 to the right of the plane P and the fact that the terminal ends (unnumbered) of the second end portions 14, 17 at all times cross the plane P, but these are inconsequential to the function and effect of the nucleus splitter 10.

Furthermore, the arms 11, 12 including the elongated narrow members 31, 32 also remain to the same side of the plane P when the forces F1, F2, (FIG. 3) are applied thereto, as is readily apparent by comparing FIGS. 2 and 3 of the drawings.

When it is desired to split or fracture a nucleus, the tips 34, 37 are introduced into the eye through the small incision when the nucleus splitter 10 is in the position/condition shown in FIG. 2, namely, in the absence of the forces F1, F2. The tips 34, 37 are inserted into one of the two previously sculpted cross grooves and the forces F1, F2 (FIG. 3) are then applied by the surgeon by simply squeezing the medial portions 15, 18 between his thumb T and forefinger F. The latter causes the progressive pivoting or rocking of the elongated narrow members 31 32 about the pivot 21 which in turn progressively spreads the tips 34, 37 defining a progressively widening acute angle A between the surfaces 33, 36 as the same progressively spread. This spreading causes opposite reaction forces R1, R2 (FIG. 4) to react against the nucleus resulting in its splitting or fracture. Once split in halve, the same process is repeated to split the remaining two halves, once again to form four quadrants.

It is particularly important to note that since the narrow elongated members 31, 32 are pivoted at 21, they cannot bodily spread laterally and When the forces F1, F2 are applied, maximum spreading of occurs at the tips 34, 37 and no spreading occurs in the area of the pivot pin 21 or the boss 40. Since the entry incision or wound is in the area of the pivot 21 and the boss 40, when the tips 34, 37 are in the sculpted groove(s) during the splitting operation, the incision will not be enlarged because there is virtually an absence of movement, lateral or otherwise, in the area of the pivot 21 and essentially over the entire longitudinal length of the boss 40. In this manner, nuclei can be cracked by utilizing a smaller entrance incision than that heretofore thought possible and in the absence of tearing or otherwise enlarging the same.

Although a preferred embodiment of the invention has been specifically illustrated and described herein, it is to be understood that minor variations may be made in the apparatus without departing from the spirit and scope of the invention, as defined the appended claims.

I claim:

1. A nucleus splitter sized and configured to crack a hard nucleus of an eye after the latter has been sculpted by a pair of crossing grooves to form quadrants comprising a pair of arms, said arms each having opposite first and second end portions and a medial portion therebetween, said arms being united at a pivot located between the first portions and the medial portions, said pivot having a pivot axis, said first end portions each being a relatively elongated narrow member, said elongated narrow members each including opposing adjacent face surfaces and nonopposing lateral edge surfaces, each lateral edge surface ending in a nucleus splitting tip having a lateral axis of projection generally parallel to the pivot axis, said second end portions being generally resilient and normally urging said narrow members and tips into abutment with each other along a plane generally through said pivot axis, said arms first end portions including the elongated narrow member and tips thereof each lying at all times generally on opposite sides of said plane, forces applied to said second end portions and directed toward each other cause said elongated narrow members to spread apart through said pivot and define an acute angle opening in a direction away from said pivot and from said second end portions, said pivot being effective for preventing lateral movement of said elongated narrow members thereby allowing insertion of said splitting tips into associated nucleus grooves through the most minimum of access incisions and, one of said arms including a generally rectangular boss received in a generally rectangular groove of the other of said arms thereby assuring guidance and alignment during movement of said elongated narrow members relative to said plane.

2. A nucleus splitter sized and configured to crack a hard nucleus of an eye after the latter has been sculpted by a pair of crossing grooves to form quadrants comprising a pair of arms, said arms each having opposite first and second end portions and a medial portion therebetween, said arms being united at a pivot located between the first portions and the medial portions, said pivot having a pivot axis, said first end portions each being a relatively elongated narrow member, said elongated narrow members each including opposing adjacent face surfaces and nonopposing lateral edge surfaces, each lateral edge surface ending in a nucleus splitting tip having a lateral axis of projection generally parallel to the pivot axis, said second end portions being generally resilient and normally urging said narrow members and tips into abutment with each other along a plane generally through said pivot axis, said arms first end portions including the elongated narrow member and tips thereof each lying at all times generally on opposite sides of said plane, forces applied to said second end portions and directed toward each other cause said elongated narrow members to spread apart through said pivot and define an acute angle opening in a direction away from said pivot and from said second end portions, said pivot being effective for preventing lateral movement of said elongated narrow members thereby allowing insertion of said splitting tips into associated nucleus grooves through the most minimum of access incisions, said tips project in the same direction and are generally of the same size, and one of said arms including a generally rectangular boss received in a generally rectangular groove of the other of said arms thereby assuring guidance and alignment during movement of said elongated narrow members relative to said plane.

3. A nucleus splitter sized and configured to crack a hard nucleus of an eye after the latter has been sculpted by a pair of crossing grooves to form quadrants comprising a pair of arms, said arms each having opposite first and second end portions and a medial portion therebetwen, said arms being united at a pivot located between the first portions and the medial portions, said pivot having a pivot axis, said first end portions each being a relatively elongated narrow member, said elongated narrow members including opposing adjacent face surfaces and nonopposing lateral edge surfaces, each lateral edge surface ending in a nucleus splitting tip having a lateral axis of projection generally parallel to the pivot axis, said second end portions being generally resilient and normally urging said narrow members and tips into peripherally coincident over-lapped side-by-side abutment with each other along a plane generally through said pivot axis, said arms first end portions including the elongated narrow member and tips thereof each lying at all times generally on opposite sides of said plane, and forces applied to said second end portions and directed toward each other cause said elongated narrow members to spread apart through said pivot and define an acute angle opening in a direction away from said pivot and from said second end portions.

4. The nucleus splitter as defined in claim 3 wherein one of said arms includes a generally rectangular boss received in a generally rectangular groove of the other of said arms thereby assuring guidance and alignment during movement of said elongated narrow members relative to said plane.

5. A nucleus splitter sized and configured to crack a hard nucleus of an eye after the latter has been sculpted by a pair of crossing grooves to form quadrants comprising a pair of arms, said arms each having opposite first and second end portions and a medial portion therebetween, said arms being united at a pivot located between the first portions and the medial portions, said pivot having a pivot axis, said first end portions each being a relatively elongated narrow member; said arms each including opposing adjacent face surfaces, opposite nonopposing face surfaces and opposite pairs of nonopposing lateral edge surfaces, adjacent lateral edge surfaces of said narrow members ending in a nucleus splitting tip having a lateral axis of projection generally parallel to the pivot axis, said second end portions being generally resilient and normally urging said narrow members and tips into abutment with each other along a plane generally through said pivot axis, said arms first end portions including the elongated narrow member and tips thereof each lying at all times generally on opposite sides of said plane, forces applied to said second end portions and directed toward each other cause said arms to spread apart through said pivot and define an acute angle opening in a direction away from said pivot and from said second end portions, and one of said elongated narrow members including a boss projecting from one of its opposing adjacent face surfaces which is received in a generally complementary contoured groove opening through the opposing adjacent face surface of the other of said arms thereby assuring guidance and alignment during movement of said elongated narrow members relative to said plane.

6. The nucleus splitter as defined in claim 5 wherein said boss is of a generally polygonal cross-sectional configuration.

7. The nucleus splitter as defined in claim 5 wherein said first end portions have faces normal to said pivot axis in abutment with each other for preventing lateral movement of said elongated narrow members thereby allowing insertion of said splitting tips into associated nucleus grooves through the most minimum of access incisions.

8. The nucleus splitter as defined in claim 5 wherein said boss has a generally planar surface normal to said pivot axis in abutment with a generally planar surface of said groove which are effective for preventing lateral movement of said elongated narrow members thereby allowing insertion of said splitting tips into associated nucleus grooves through the most minimum of access incisions.

9. A nucleus splitter sized and configured to crack a hard nucleus of an eye after the latter has been sculpted by a pair of crossing grooves to form quadrants comprising a pair of arms, said arms each having opposite first and second end portions and a medial portion therebetween, said arms being united at a pivot located between the first portions and the medial portions, said pivot having a pivot axis, said first end portions each being a relatively elongated narrow member, said arms including opposing adjacent face surfaces and nonopposing lateral edge surfaces, each lateral edge surface ending in a nucleus splitting tip having a lateral axis of projection generally parallel to the pivot axis, said second end portions being generally resilient and normally urging said narrow members and tips into peripherally coincident over-lapped side-by-side abutment with each other along a plane generally through said pivot axis, said arms first end portions including the elongated narrow member and tips thereof each lying at all times generally on opposite sides of said plane, forces applied to said second end portions and directed toward each other cause said elongated narrow members to spread apart through said pivot and define an acute angle opening in a direction away from said pivot and from said second end portions, one of said arms having a boss and the other of said arms having a complementary contoured groove, said boss having a generally planar surface normal to said pivot axis in abutment with a generally planar surface of said groove which are effective for preventing lateral movement of said elongated narrow members thereby allowing insertion of said splitting tips into associated nucleus grooves through the most minimum of access incisions.

* * * * *